(12) United States Patent
West

(10) Patent No.: US 7,759,475 B2
(45) Date of Patent: *Jul. 20, 2010

(54) ENZYME EXPRESSION METHODS AND COMPOSITIONS

(75) Inventor: Brian West, San Francisco, CA (US)

(73) Assignee: Plexxikon, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/409,443

(22) Filed: Mar. 23, 2009

(65) Prior Publication Data

US 2009/0191586 A1 Jul. 30, 2009

Related U.S. Application Data

(62) Division of application No. 11/015,730, filed on Dec. 16, 2004, now Pat. No. 7,517,970.

(60) Provisional application No. 60/530,944, filed on Dec. 19, 2003.

(51) Int. Cl.
C07J 21/02 (2006.01)
C12N 9/00 (2006.01)
C12P 21/04 (2006.01)
C07H 21/04 (2006.01)
C12N 1/12 (2006.01)

(52) U.S. Cl. ............... 536/23.1; 435/183; 435/69.7; 435/70.1; 435/71.1; 435/252.1

(58) Field of Classification Search .............. None
See application file for complete search history.

(56) References Cited

U.S. PATENT DOCUMENTS

| 5,721,118 | A | 2/1998 | Scheffler |
| 6,025,155 | A | 2/2000 | Hadlaczky et al. |
| 2005/0069975 | A1 | 3/2005 | Atwell et al. |

OTHER PUBLICATIONS

Brown et al., The Journal of Biological Chemistry, 274(18): 8746-8756 (1999).
Grangeasse et al., The Journal of Biological Chemistry, 278(41): 39323-39329 (2003).
Matsui et al., Biochemical and Biophysical Research Communications, 284: 798-807 (2001).
Mijakovic et al., EMBO Journal, 22(18):4709-4718 (2003).
Palka et al., The Journal of Biological Chemistry, 278(8): 5728-5735 (2003).
Weijland et al., Eur. J. Biochem., 240: 756-764 (1996).
Zhuo et al., The Journal of Biological Chemistry, 268(24): 17754-17761 (1993).
Zhuo et al., The Journal of Biological Chemistry, 269(42): 26234-26238 (1994).
Oudot et al., The isocitrate dehydrogenase kinase/phosphatase from *Escherichia coli* is highly sensitive to in-vitro oxidative conditions. Eur. Jo. Biochem., 262: 224-229, 1999.
Schiering et al., Crystal structure of the tyrosine kinase domain of the hepatocyte growth factor receptor c-Met and its complex with the microbial alkaloid K-252a. PNAS, 100(22): 12654-12659, 2003.
Ma et al., c-Met: Structure, functions and potential for therapeutic inhibition. Cancer and Metastasis Reviews, 22:309-325, 2003.
International Search Report for PCT Application PCT/US2004/42776.
Hafner et al., "Isothermal Amplification and Multimerization of DNA by *Bst* DNA Polyerase" *Biotechniques* 30:852-867 (2001).
Kern and Hampton, "Direct Hybridization of Large-Insert Genomic Clones on High-Density Gridded cDNA Filter Arrays" *Biotechniques* 23:120-124 (1997).
Roberts et al., "Generation of an Antibody With Enhanced Affinity and Specificity For Its Antigen by Protein Engineering," *Nature* 328:731-734 (1987).
Rosenfeld, M., "Human Artificial Chromosomes Get Real," *Nat. Genet.* 15:333-335 (1997).
Saiki, R., "Amplification of Genomic DNA," *PCR Protocols* 13-20 (1990).
Schneider et al., "Functional Purification of a Bacterial ATP-Binding Cassette Transporter Protein (MalK) From the Cytoplasmic Fraction of an Overproducing Stain," *Protein Expr. Purif.* 6435:10 (1995).
Wharam et al., "Specific Detection of DNA and RNA Targets Using a Novel Isothermal Nucleic Acid Amplification Assay Based on the Formation of a Three-Way Junction Structure," *Nucleic Acids Res.* 29(11):1-8 (2001).
Woon et al., "Construction and Characterization of a 10-Fold Genome Equivalent Rat P1-Derived Artificial Chromosome Library," *Genomics* 50:306-316 (1998).
Goodsell, S.D. The Oncologist, 2005, 10:758-759.
New England BioLabs Product Catalog description for Lambda Phosphatase, pp. 1-3. No. date.
Maulik et al., Cytokine and Growth Factors Reviews, 2002, 13:41-59.
Kholod et al., BioTechniques, 2004, 31(2), pp. 322-328.
Brenda search results for kinases and phosphatase. No date.

*Primary Examiner*—Suzanne M. Noakes
(74) *Attorney, Agent, or Firm*—Foley & Lardner LLP

(57) ABSTRACT

Methods for expressing active enzymes are described that involve co-expressing a first enzyme with a second enzyme that has an enzymatic activity that reverses a modification on the first enzyme and/or for identification of soluble and/or active catalytic domains by systematic variation of fragment lengths around catalytic domain boundaries.

24 Claims, 1 Drawing Sheet

SEQUENCE LISTING

<160> NUMBER OF SEQ ID NOS: 24

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgcgaagtc gacgaaggag atatatccat ggagatggaa aaggagttcg                50

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcgaagaa ttctcacccc atgatgaatt tggcacct                            38

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      His tag

<400> SEQUENCE: 3

Met Gly His His His His His His
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      His tag

<400> SEQUENCE: 4

Met Gly His His His His His His Met
  1               5

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaattagttc atatggatgc aagagtacac actcctca                            38

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
tttcctgcat atgaaaaaga gaaagcaaat taaagatct                              39

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aactacacat atggtttcaa aatgaatctg tagactac                               38

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcatctcat atgggttcat gccgacaagt gcag                                   34

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctgacacat atgtccccca tcctaactag tgg                                    33

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
catcctacat atgggggact ctgatatatc cagtc                                  35

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcagctacat atggctctaa atccagagct ggtcat                                 36

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 12
tgctctacat atggagctgg tccaggcagt gca                                    33

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcagctacat atgggaagag ggcattttgg ttgtgt                                 36

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcagctacat atgccattac tgcaaaatac tgtccac                                37

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacaagtcga ctaaatgaaa gtagagaaga tcgctg                                 36

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctagcaggtc gactacccaa tgaaagtaga gaagatcgc                              39

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctagcaggtc gactactccc caatgaaagt agagaagat                              39

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
```

-continued

```
aggatccgtc gactatgatg tctcccagaa ggag                                    34

<210> SEQ ID NO 19
<211> LENGTH: 1937
<212> TYPE: DNA
<213> ORGANISM: Artificial Sequence
<220> FEATURE:
<221> NAME/KEY: CDS
<222> LOCATION: (88)..(978)
<220> FEATURE:
<221> NAME/KEY: CDS
<222> LOCATION: (1003)..(1851)
<220> FEATURE:
<223> OTHER INFORMATION: Description of Artificial Sequence: Synthetic
      construct

<400> SEQUENCE: 19
taatacgact cactataggg gaattgtgag cggataacaa ttcccctcta gaaataattt       60
tgtttaactt taagaaggag atatacc atg ggt cac cac cat cac cac cac ggt      114
                              Met Gly His His His His His His Gly
                                1               5 gtg tcc ccc aac tac gac aag tgg gag atg gaa cgc acg gac atc acc        162
Val Ser Pro Asn Tyr Asp Lys Trp Glu Met Glu Arg Thr Asp Ile Thr
 10              15                  20                  25 atg aag cac aag ctg ggc ggg ggc cag tac ggg gag gtg tac gag ggc        210
Met Lys His Lys Leu Gly Gly Gly Gln Tyr Gly Glu Val Tyr Glu Gly
             30                  35                  40 gtg tgg aag aaa tac agc ctg acg gtg gcc gtg aag acc ttg aag gag        258
Val Trp Lys Lys Tyr Ser Leu Thr Val Ala Val Lys Thr Leu Lys Glu
         45                  50                  55 gac acc atg gag gtg gaa gag ttc ttg aaa gaa gct gca gtc atg aaa        306
Asp Thr Met Glu Val Glu Glu Phe Leu Lys Glu Ala Ala Val Met Lys
     60                  65                  70 gag atc aaa cac cct aac ctg gtg cag ctc ctt ggg gtc tgc acc cgg        354
Glu Ile Lys His Pro Asn Leu Val Gln Leu Leu Gly Val Cys Thr Arg
 75                  80                  85 gag ccc ccg ttc tat atc atc act gag ttc atg acc tac ggg aac ctc        402
Glu Pro Pro Phe Tyr Ile Ile Thr Glu Phe Met Thr Tyr Gly Asn Leu
 90                  95                 100                 105 ctg gac tac ctg agg gag tgc aac cgg cag gag gtg aac gcc gtg gtg        450
Leu Asp Tyr Leu Arg Glu Cys Asn Arg Gln Glu Val Asn Ala Val Val
            110                 115                 120 ctg ctg tac atg gcc act cag atc tcg tca gcc atg gag tac ctg gag        498
Leu Leu Tyr Met Ala Thr Gln Ile Ser Ser Ala Met Glu Tyr Leu Glu
        125                 130                 135 aag aaa aac ttc atc cac aga gat ctt gct gcc cga aac tgc ctg gta        546
Lys Lys Asn Phe Ile His Arg Asp Leu Ala Ala Arg Asn Cys Leu Val
    140                 145                 150 ggg gag aac cac ttg gtg aag gta gct gat ttt ggc ctg agc agg ttg        594
Gly Glu Asn His Leu Val Lys Val Ala Asp Phe Gly Leu Ser Arg Leu
155                 160                 165 atg aca ggg gac acc tac aca gcc cat gct gga gcc aag ttc ccc atc        642
Met Thr Gly Asp Thr Tyr Thr Ala His Ala Gly Ala Lys Phe Pro Ile
170                 175                 180                 185 aaa tgg act gca ccc gag agc ctg gcc tac aac aag ttc tcc atc aag        690
Lys Trp Thr Ala Pro Glu Ser Leu Ala Tyr Asn Lys Phe Ser Ile Lys
                190                 195                 200 tcc gac gtc tgg gca ttt gga gta ttg ctt tgg gaa att gct acc tat        738
Ser Asp Val Trp Ala Phe Gly Val Leu Leu Trp Glu Ile Ala Thr Tyr
            205                 210                 215 ggc atg tcc cct tac ccg gga att gac ctg tcc cag gtg tat gag ctg        786
```

```
Gly Met Ser Pro Tyr Pro Gly Ile Asp Leu Ser Gln Val Tyr Glu Leu
            220                 225                 230 cta gag aag gac tac cgc atg gag cgc cca gaa ggc tgc cca gag aag      834
Leu Glu Lys Asp Tyr Arg Met Glu Arg Pro Glu Gly Cys Pro Glu Lys
235                 240                 245 gtc tat gaa ctc atg cga gca tgt tgg cag tgg aat ccc tct gac cgg      882
Val Tyr Glu Leu Met Arg Ala Cys Trp Gln Trp Asn Pro Ser Asp Arg
250                 255                 260                 265 ccc tcc ttt gct gaa atc cac caa gcc ttt gaa aca atg ttc cag gaa      930
Pro Ser Phe Ala Glu Ile His Gln Ala Phe Glu Thr Met Phe Gln Glu
                270                 275                 280 tcc agt atc tca gac gaa gtg gaa aag gag ctg ggg aaa caa ggc gtc      978
Ser Ser Ile Ser Asp Glu Val Glu Lys Glu Leu Gly Lys Gln Gly Val
            285                 290                 295 tgagtcgacg aaggagatat atcc atg gag atg gaa aag gag ttc gag cag      1029
                          Met Glu Met Glu Lys Glu Phe Glu Gln
                                      300                 305 atc gac aag tcc ggg agc tgg gcg gcc att tac cag gat atc cga cat      1077
Ile Asp Lys Ser Gly Ser Trp Ala Ala Ile Tyr Gln Asp Ile Arg His
                310                 315                 320 gaa gcc agt gac ttc cca tgt aga gtg gcc aag ctt cct aag aac aaa      1125
Glu Ala Ser Asp Phe Pro Cys Arg Val Ala Lys Leu Pro Lys Asn Lys
            325                 330                 335 aac cga aat agg tac aga gac gtc agt ccc ttt gac cat agt cgg att      1173
Asn Arg Asn Arg Tyr Arg Asp Val Ser Pro Phe Asp His Ser Arg Ile
340                 345                 350 aaa cta cat caa gaa gat aat gac tat atc aac gct agt ttg ata aaa      1221
Lys Leu His Gln Glu Asp Asn Asp Tyr Ile Asn Ala Ser Leu Ile Lys
355                 360                 365                 370 atg gaa gaa gcc caa agg agt tac att ctt acc cag ggc cct ttg cct      1269
Met Glu Glu Ala Gln Arg Ser Tyr Ile Leu Thr Gln Gly Pro Leu Pro
                375                 380                 385 aac aca tgc ggt cac ttt tgg gag atg gtg tgg gag cag aaa agc agg      1317
Asn Thr Cys Gly His Phe Trp Glu Met Val Trp Glu Gln Lys Ser Arg
            390                 395                 400 ggt gtc gtc atg ctc aac aga gtg atg gag aaa ggt tcg tta aaa tgc      1365
Gly Val Val Met Leu Asn Arg Val Met Glu Lys Gly Ser Leu Lys Cys
                405                 410                 415 gca caa tac tgg cca caa aaa gaa gaa aaa gag atg atc ttt gaa gac      1413
Ala Gln Tyr Trp Pro Gln Lys Glu Glu Lys Glu Met Ile Phe Glu Asp
            420                 425                 430 aca aat ttg aaa tta aca ttg atc tct gaa gat atc aag tca tat tat      1461
Thr Asn Leu Lys Leu Thr Leu Ile Ser Glu Asp Ile Lys Ser Tyr Tyr
435                 440                 445                 450 aca gtg cga cag cta gaa ttg gaa aac ctt aca acc caa gaa act cga      1509
Thr Val Arg Gln Leu Glu Leu Glu Asn Leu Thr Thr Gln Glu Thr Arg
                455                 460                 465 gag atc tta cat ttc cac tat acc aca tgg cct gac ttt gga gtc cct      1557
Glu Ile Leu His Phe His Tyr Thr Thr Trp Pro Asp Phe Gly Val Pro
            470                 475                 480 gaa tca cca gcc tca ttc ttg aac ttt ctt ttc aaa gtc cga gag tca      1605
Glu Ser Pro Ala Ser Phe Leu Asn Phe Leu Phe Lys Val Arg Glu Ser
                485                 490                 495 ggg tca ctc agc ccg gag cac ggg ccc gtt gtg gtg cac tgc agt gca      1653
Gly Ser Leu Ser Pro Glu His Gly Pro Val Val Val His Cys Ser Ala
            500                 505                 510 ggc atc ggc agg tct gga acc ttc tgt ctg gct gat acc tgc ctc ttg      1701
Gly Ile Gly Arg Ser Gly Thr Phe Cys Leu Ala Asp Thr Cys Leu Leu
515                 520                 525                 530
```

```
ctg atg gac aag agg aaa gac cct tct tcc gtt gat atc aag aaa gtg      1749
Leu Met Asp Lys Arg Lys Asp Pro Ser Ser Val Asp Ile Lys Lys Val
                535                 540                 545 ctg tta gaa atg agg aag ttt cgg atg ggg ctg atc cag aca gcc gac      1797
Leu Leu Glu Met Arg Lys Phe Arg Met Gly Leu Ile Gln Thr Ala Asp
            550                 555                 560 cag ctg cgc ttc tcc tac ctg gct gtg atc gaa ggt gcc aaa ttc atc      1845
Gln Leu Arg Phe Ser Tyr Leu Ala Val Ile Glu Gly Ala Lys Phe Ile
        565                 570                 575 atg ggg tgagaattcg aggccagcag ggccaccgct gagcaataac tagcataacc       1901
Met Gly
    580 ccttggggcc tctaaacggt cttgaggggt tttttg                              1937

<210> SEQ ID NO 20
<211> LENGTH: 435
<212> TYPE: PRT
<213> ORGANISM: Homo sapiens

<400> SEQUENCE: 20

Met Glu Met Glu Lys Glu Phe Glu Gln Ile Asp Lys Ser Gly Ser Trp
 1               5                  10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285
```

Asp Gln Trp Lys Glu Leu Ser His Glu Asp Leu Glu Pro Pro Glu
    290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Lys Gly Ser
            340                 345                 350

Pro Leu Asn Ala Ala Pro Tyr Gly Ile Glu Ser Met Ser Gln Asp Thr
                355                 360                 365

Glu Val Arg Ser Arg Val Val Gly Gly Ser Leu Arg Gly Ala Gln Ala
    370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
                420                 425                 430

Ser Asn Thr
        435

<210> SEQ ID NO 21
<211> LENGTH: 3318
<212> TYPE: DNA
<213> ORGANISM: Homo sapiens

<400> SEQUENCE: 21

| | | |
|---|---|---|
| gtgatgcgta gttccggctg ccggttgaca tgaagaagca gcagcggcta gggcggcggt | 60 |
| agctgcaggg gtcggggatt gcagcgggcc tcggggctaa gagcgcgacg cggcctagag | 120 |
| cggcagacgc gcagtgggc cgagaaggag gcgcagcagc cgccctggcc cgtcatggag | 180 |
| atggaaaagg agttcgagca gatcgacaag tccgggagct gggcggccat ttaccaggat | 240 |
| atccgacatg aagccagtga cttcccatgt agagtggcca agcttcctaa gaacaaaaac | 300 |
| cgaaataggt acagagacgt cagtcccttt gaccatagtc ggattaaact acatcaagaa | 360 |
| gataatgact atatcaacgc tagtttgata aaaatggaag aagcccaaag gagttacatt | 420 |
| cttacccagg gcccttttgcc taacacatgc ggtcactttt gggagatggt gtgggagcag | 480 |
| aaaagcaggg gtgtcgtcat gctcaacaga gtgatggaga aggttcgtt aaaatgcgca | 540 |
| caatactggc cacaaaaaga agaaaaagag atgatctttg aagacacaaa tttgaaatta | 600 |
| acattgatct ctgaagatat caagtcatat tatacagtgc gacagctaga attggaaaac | 660 |
| cttacaaccc aagaaactcg agagatctta catttccact ataccacatg gcctgacttt | 720 |
| ggagtccctg aatcaccagc ctcattcttg aactttcttt tcaaagtccg agagtcaggg | 780 |
| tcactcagcc cggagcacgg gccgttgtg gtgcactgca gtgcaggcat cggcaggtct | 840 |
| ggaaccttct gtctggctga tacctgcctc ttgctgatgg acaagaggaa agacccttct | 900 |
| tccgttgata tcaagaaagt gctgttagaa atgaggaagt ttcggatggg gctgatccag | 960 |
| acagccgacc agctgcgctt ctcctacctg gctgtgatcg aaggtgccaa attcatcatg | 1020 |
| ggggactctt ccgtgcagga tcagtggaag gagctttccc acgaggacct ggagcccca | 1080 |
| cccgagcata tcccccccacc tccccggcca cccaaacgaa tcctggagcc acacaatggg | 1140 |
| aaatgcaggg agttcttccc aaatcaccag tgggtgaagg aagagaccca ggaggataaa | 1200 |

```
gactgcccca tcaaggaaga aaaaggaagc cccttaaatg ccgcaccctca cggcatcgaa    1260 agcatgagtc aagacactga agttagaagt cgggtcgtgg ggggaagtct tcgaggtgcc    1320
caggctgcct ccccagccaa aggggagccg tcactgcccg agaaggacga ggaccatgca    1380
ctgagttact ggaagccctt cctggtcaac atgtgcgtgg ctacggtcct cacggccggc    1440
gcttacctct gctacaggtt cctgttcaac agcaacacat agcctgaccc tcctccactc    1500
cacctccacc cactgtccgc ctctgcccgc agagcccacg cccgactagc aggcatgccg    1560
cggtaggtaa gggccgccgg accgcgtaga gagccgggcc ccggacggac gttggttctg    1620
cactaaaacc catcttcccc ggatgtgtgt ctcaccccctc atccttttac tttttgcccc    1680
ttccactttg agtaccaaat ccacaagcca ttttttgagg agagtgaaag agagtaccat    1740
gctggcggcg cagagggaag gggcctacac ccgtcttggg gctcgcccca cccagggctc    1800
cctcctggag catcccaggc gggcggcacg ccaacagccc ccccttgaa tctgcaggga    1860 gcaactctcc actccatatt tatttaaaca atttttccc caaaggcatc catagtgcac    1920
tagcattttc ttgaaccaat aatgtattaa aattttttga tgtcagcctt gcatcaaggg    1980
ctttatcaaa aagtacaata ataaatcctc aggtagtact gggaatggaa ggctttgcca    2040
tgggcctgct gcgtcagacc agtactggga aggaggacgg ttgtaagcag ttgttattta    2100
gtgatattgt gggtaacgtg agaagataga acaatgctat aatatataat gaacacgtgg    2160
gtatttaata agaaacatga tgtgagatta ctttgtcccg cttattctcc tccctgttat    2220
ctgctagatc tagttctcaa tcactgctcc ccgtgtgta ttagaatgca tgtaaggtct    2280
tcttgtgtcc tgatgaaaaa tatgtgcttg aaatgagaaa ctttgatctc tgcttactaa    2340
tgtgccccat gtccaagtcc aacctgcctg tgcatgacct gatcattaca tggctgtggt    2400
tcctaagcct gttgctgaag tcattgtcgc tcagcaatag ggtgcagttt tccaggaata    2460
ggcatttgcc taattcctgg catgacactc tagtgacttc ctggtgaggc ccagcctgtc    2520
ctggtacagc agggtcttgc tgtaactcag acattccaag ggtatgggaa gccatattca    2580
cacctcacgc tctggacatg atttagggaa gcaggacac ccccgcccc ccacctttgg    2640 gatcagcctc cgccattcca agtcaacact cttcttgagc agaccgtgat ttggaagaga    2700
ggcacctgct ggaaaccaca cttcttgaaa cagcctgggt gacggtcctt taggcagcct    2760
gccgccgtct ctgtcccggt tcaccttgcc gagagaggcg cgtctgcccc accctcaaac    2820 cctgtgggggc ctgatggtgc tcacgactct tcctgcaaag ggaactgaag acctccacat    2880
taagtggctt tttaacatga aaaacacggc agctgtagct cccgagctac tctcttgcca    2940 gcatttttcac attttgcctt tctcgtggta gaagccagta cagagaaatt ctgtggtggg    3000
aacattcgag gtgtcaccct gcagagctat ggtgaggtgt ggataaggct taggtgccag    3060
gctgtaagca ttctgagctg ggcttgttgt ttttaagtcc tgtatatgta tgtagtagtt    3120
tgggtgtgta tatatagtag catttcaaaa tggacgtact ggtttaacct cctatccttg    3180
gagagcagct ggctctccac cttgttacac attatgttag agaggtagcg agctgctctg    3240
ctatatgcct taagccaata tttactcatc aggtcattat ttttttacaat ggccatggaa    3300 taaaccattt ttacaaaa                                                  3318
```

<210> SEQ ID NO 22
<211> LENGTH: 221
<212> TYPE: PRT
<213> ORGANISM: Bacteriophage lambda

<400> SEQUENCE: 22

```
Met Arg Tyr Tyr Glu Lys Ile Asp Gly Ser Lys Tyr Arg Asn Ile Trp
 1               5                  10                  15

Val Val Gly Asp Leu His Gly Cys Tyr Thr Asn Leu Met Asn Lys Leu
             20                  25                  30

Asp Thr Ile Gly Phe Asp Asn Lys Asp Leu Leu Ile Ser Val Gly
             35                  40                  45

Asp Leu Val Asp Arg Gly Ala Glu Asn Val Glu Cys Leu Glu Leu Ile
 50                  55                  60

Thr Phe Pro Trp Phe Arg Ala Val Arg Gly Asn His Glu Gln Met Met
 65                  70                  75                  80

Ile Asp Gly Leu Ser Glu Arg Gly Asn Val Asn His Trp Leu Leu Asn
                 85                  90                  95

Gly Gly Gly Trp Phe Phe Asn Leu Asp Tyr Asp Lys Glu Ile Leu Ala
             100                 105                 110

Lys Ala Leu Ala His Lys Ala Asp Glu Leu Pro Leu Ile Ile Glu Leu
             115                 120                 125

Val Ser Lys Asp Lys Lys Tyr Val Ile Cys His Ala Asp Tyr Pro Phe
 130                 135                 140

Asp Glu Tyr Glu Phe Gly Lys Pro Val Asp His Gln Gln Val Ile Trp
145                 150                 155                 160

Asn Arg Glu Arg Ile Ser Asn Ser Gln Asn Gly Ile Val Lys Glu Ile
                 165                 170                 175

Lys Gly Ala Asp Thr Phe Ile Phe Gly His Thr Pro Ala Val Lys Pro
             180                 185                 190

Leu Lys Phe Ala Asn Gln Met Tyr Ile Asp Thr Gly Ala Val Phe Cys
     195                 200                 205

Gly Asn Leu Thr Leu Ile Gln Val Gln Gly Glu Gly Ala
         210                 215                 220

<210> SEQ ID NO 23
<211> LENGTH: 297
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 23

Met Gly His His His His His Gly Val Ser Pro Asn Tyr Asp Lys
 1               5                  10                  15

Trp Glu Met Glu Arg Thr Asp Ile Thr Met Lys His Lys Leu Gly Gly
             20                  25                  30

Gly Gln Tyr Gly Glu Val Tyr Glu Gly Val Trp Lys Lys Tyr Ser Leu
             35                  40                  45

Thr Val Ala Val Lys Thr Leu Lys Glu Asp Thr Met Glu Val Glu Glu
 50                  55                  60

Phe Leu Lys Glu Ala Ala Val Met Lys Glu Ile Lys His Pro Asn Leu
 65                  70                  75                  80

Val Gln Leu Leu Gly Val Cys Thr Arg Glu Pro Pro Phe Tyr Ile Ile
                 85                  90                  95

Thr Glu Phe Met Thr Tyr Gly Asn Leu Leu Asp Tyr Leu Arg Glu Cys
             100                 105                 110

Asn Arg Gln Glu Val Asn Ala Val Val Leu Leu Tyr Met Ala Thr Gln
             115                 120                 125

Ile Ser Ser Ala Met Glu Tyr Leu Glu Lys Lys Asn Phe Ile His Arg
```

```
            130                 135                 140
Asp Leu Ala Ala Arg Asn Cys Leu Val Gly Glu Asn His Leu Val Lys
145                 150                 155                 160

Val Ala Asp Phe Gly Leu Ser Arg Leu Met Thr Gly Asp Thr Tyr Thr
                165                 170                 175

Ala His Ala Gly Ala Lys Phe Pro Ile Lys Trp Thr Ala Pro Glu Ser
            180                 185                 190

Leu Ala Tyr Asn Lys Phe Ser Ile Lys Ser Asp Val Trp Ala Phe Gly
                195                 200                 205

Val Leu Leu Trp Glu Ile Ala Thr Tyr Gly Met Ser Pro Tyr Pro Gly
    210                 215                 220

Ile Asp Leu Ser Gln Val Tyr Glu Leu Leu Glu Lys Asp Tyr Arg Met
225                 230                 235                 240

Glu Arg Pro Glu Gly Cys Pro Glu Lys Val Tyr Glu Leu Met Arg Ala
                245                 250                 255

Cys Trp Gln Trp Asn Pro Ser Asp Arg Pro Ser Phe Ala Glu Ile His
            260                 265                 270

Gln Ala Phe Glu Thr Met Phe Gln Glu Ser Ser Ile Ser Asp Glu Val
                275                 280                 285

Glu Lys Glu Leu Gly Lys Gln Gly Val
            290                 295

<210> SEQ ID NO 24
<211> LENGTH: 283
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
                20                  25                  30

Arg Val Ala Lys Leu Pro Lys Asn Lys Asn Arg Asn Arg Tyr Arg Asp
            35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
                100                 105                 110

Val Met Glu Lys Gly Ser Leu Lys Cys Ala Gln Tyr Trp Pro Gln Lys
            115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
                180                 185                 190
```

```
Asn Phe Leu Phe Lys Val Arg Glu Ser Gly Ser Leu Ser Pro Glu His
        195                 200                 205
Gly Pro Val Val His Cys Ser Ala Gly Ile Gly Arg Ser Gly Thr
    210             215                 220
Phe Cys Leu Ala Asp Thr Cys Leu Leu Leu Met Asp Lys Arg Lys Asp
225             230                 235                 240
Pro Ser Ser Val Asp Ile Lys Lys Val Leu Leu Glu Met Arg Lys Phe
                245                 250                 255
Arg Met Gly Leu Ile Gln Thr Ala Asp Gln Leu Arg Phe Ser Tyr Leu
            260                 265                 270
Ala Val Ile Glu Gly Ala Lys Phe Ile Met Gly
            275             280
```

ENZYME EXPRESSION METHODS AND COMPOSITIONS

CROSS-REFERENCE TO RELATED PATENT APPLICATIONS

This application is a divisional application of U.S. Nonprovisional application Ser. No. 11/015,730, filed Dec. 16, 2004, now U.S. Pat. No. 7,517,970, which claims the benefit of U.S. Provisional Application 60/530,944, filed Dec. 19, 2003, which is incorporated herein by reference in its entirety, including drawings.

BACKGROUND OF THE INVENTION

The present invention relates to the field of expression of enzymes and fragments of enzymes.

For many applications, it is advantageous to express recombinant enzymes, which may be full-length enzymes or fragments of such full-length enzymes, e.g., catalytic domains. However, in some cases, expression of such an enzyme results in an unacceptable or variable level of modification of the enzyme, such as by self-modification or by modification by host enzymes.

In addition, in some cases attempts to express a recombinant enzyme results in insoluble and/or inactive enzyme. Such difficulties can arise, for example, when expressing eukaryotic coding sequences in a prokaryotic expression system such as E. coli.

SUMMARY OF THE INVENTION

The present invention concerns the provisions of polypeptides that have reduced levels of, or are free from, particular enzymatic modifications, especially attachment of modification moieties, and thus provides a method for expressing an enzyme that has a reduced level of a modification moiety, such as phosphate groups. Such a method is useful in a variety of different contexts. For example, phosphate modifications are often involved in activation of enzymes that have a signaling or signal amplification function, such as many different kinases. In other cases, a modification may occur at very high levels in the expression system, which can interfere with normal activity and/or normal structure. In still other cases, the presence of high modification levels may make it difficult to obtain crystals, or crystals may occur in an unnatural form due to the high density of the modifications, or crystals may contain additional molecules or ions due to the presence of added modification moieties. In such cases, as well as others, it is beneficial to reduce or even eliminate modification moieties of a particular type or types.

The present invention accomplishes the reduction in modification by co-expressing the enzyme of interest with a second enzyme that reverses or counteracts the modification, e.g., removes the modification moiety. The expression level of the second enzyme can be established at a desired level to provide a desired level of reduction of modification of the first enzyme. A particular example of such enzyme pairing is a pairing of kinase and phosphatase that have counteracting activities, e.g., protein tyrosine kinase and protein tyrosine phosphatase. In many cases, one or both of the enzymes is a fragment, e.g., a catalytic domain, of a full-length protein.

Thus, in a first aspect, the invention concerns a method for expressing a recombinant kinase domain with reduced phosphorylation by co-expressing the recombinant kinase domain with a phosphatase domain that removes phosphate groups from residues of the kinase domain. Typically the expression is in a cellular expression system.

In certain embodiments, the kinase domain and the phosphatase domain are expressed separately from a single vector; the kinase domain and the phosphatase domain are expressed from a coding sequence as a fusion protein (which can be joined with a cleavable linker to give separate proteins); the kinase domain and the phosphatase domain are expressed from a bi-cistronic mRNA; the kinase domain and the phosphatase domain are encoded by separate vectors; the kinase domain is from a protein tyrosine kinase; the phosphatase domain is from a protein tyrosine phosphatase; the kinase autophosphorylates; the kinase includes the human c-Met kinase domain; the kinase includes the human c-Abl kinase domain; the co-expression results in reduced phosphorylation on the kinase as compared to expression of the kinase domain in the same expression system in the absence of a counteracting phosphatase; the co-expression results in improved crystallization of the kinase domain as compared to expression of the kinase domain in the same expression system in the absence of a counteracting phosphatase; the co-expression results in a kinase preparation that has more uniform kinase activity as compared to in the absence of such co-expression; the co-expression results in a kinase preparation that has increased specific activity as compared to in the absence of such co-expression; the co-expression results in a kinase preparation that has improved activity as compared to in the absence of such co-expression; the co-expression results in a kinase having an increased drug inhibitor sensitivity (e.g., due to its having a state of modification giving it enzymatic and pharmacological properties that mimics the state(s) that are the best targets for drug inhibitors that can most effectively inhibit the enzyme to effect the desired physiological response in the cell or tissue or organism).

As used in connection with production of defined polypeptides, the term "expressing" refers to the process of enzymatically synthesizing a polypeptide from a nucleic acid molecule that encodes the polypeptide. In most cases, the polypeptide is expressed in a cellular system.

Similarly, "co-expressing" refers to the expression of two different polypeptides concurrently in the same expression system, typically in the same cellular expression system.

As used herein in connection with enzymes, the term "catalytic domain" refers to the portion of an enzyme where catalytic action occurs, delimited by amino acid sequence and three-dimensional structure. Thus, for a kinase, the term "kinase domain" refers to the catalytic domain where kinase activity is catalyzed. Persons skilled in the art are familiar with these terms, and catalytic domains have been identified for many enzymes.

In connection with nucleic acid coding sequences and encoded polypeptides, the term "recombinant" means that a nucleic acid sequence has been removed from its natural sequence environment and inserted in a different environment and/or a nucleic acid sequence has been associated with different regulatory sequences such that expression from the nucleic acid sequence is significantly altered.

In connection with the activities of a protein modification enzymes and an enzyme that counteracts or reverses the activity of that enzyme, the terms "reverse" and "counteract" indicate that the enzyme that counteracts or reverses the activity of the modification enzyme reduces or eliminates the modification catalyzed by the modification enzyme in a common substrate.

In the context of the present invention, the term "reduced modification" means that a particular enzymatic modification is present in substrate molecules, e.g., substrate proteins, at a lower level than in the same type of substrate molecules under comparison conditions. For example, the level of modification present on substrate protein molecules can be reduced when the substrate proteins are expressed in the presence of an enzyme that reverses the modification. Thus, the term "reduced phosphorylation" refers to a lower level of phosphate groups (or even the absence of such groups) as compared to the level of phosphate groups present under comparison conditions.

In connection with enzymatic modification of proteins, the term "modification moiety" refers to a portion of a substrate protein that is changed, typically by the addition or substitution of a chemical group, such as a phosphate group or methyl group.

In the context of protein expression, the term "cellular expression system" refers to a system for expressing a protein in a cell during culture. The protein product is typically recovered by lysing the cells and purifying the desired product from the lysate.

As used herein, the term "bi-cistronic mRNA" refers to an mRNA that can be translated to produce two independent polypeptide products (unless specifically indicated additional independent polypeptide products can also be encoded by the mRNA such that the mRNA is "polycistronic").

The term "vector" is used conventionally for molecular biology to refer to a genetic construct that is adapted for insertion of recombinant nucleic acid sequences and transfection of cells to carry the recombinant nucleic acid sequence into the cells. Thus, "expression vector" refers to a vector that is configured such that one or more polypeptides are expressed from the vector intracellularly.

The terms "protein kinase" and "protein phosphatase" are used conventionally to refer respectively to enzymes that catalyze phosphorylation and dephosphorylation of proteins. Thus, the terms "protein tyrosine kinase" refers to a protein kinase that catalyzes phosphorylation of protein substrates on tyrosine residues, while "protein tyrosine phosphatase" refers to a protein phosphatase that removes phosphate groups from tyrosine residues of substrate proteins.

In the context of the present invention, the term "self modify" indicates that a particular enzyme (which can be a catalytic domain) modifies molecules of that particular enzyme under suitable reaction conditions. Typically a molecule of the particular enzyme will modify other molecules of that same particular enzyme; it can also typically modify other substrates. Thus, the term "autophosphorylate" refers to a self-modification in which a kinase enzyme phosphorylates molecules of that same kinase.

The term "endogenous enzyme" is used to refer to an enzyme that is naturally produced in a cell. Thus, for example, in the context of the present invention, a kinase produced in a cell from a recombinant sequence may be phosphorylated by an endogenous protein kinase.

In the context of the present invention, the term "improving crystallization" indicates that the crystallizability and/or crystal quality of a polypeptide is improved under particular conditions as compared to a reference condition. For example, a polypeptide that has a uniform level of a chemical modification may crystallize more readily and/or form better quality crystals (e.g., give higher resolution diffraction pattern) than a polypeptide that is heterogeneous with respect to the level of that modification.

The phrase "more uniform activity" indicates that the enzymatic activity of repeat preparations is more consistent. The phrase "increased specific activity" refers to an increase in the enzymatic activity per milligram of the kinase protein in a preparation. The phrase "improved activity" refers to more uniform activity and/or increased specific activity. In connection with activity of an enzyme with a changed level or pattern of modification, the phrase "increased drug inhibitor sensitivity" refers to inhibition of the activity at concentrations of a drug inhibitor that would show less inhibition of a protein that is modified differently.

In the context of modifications of a polypeptide in a protein preparation, the term "homogeneity" refers to the degree to which only one species of the polypeptide is present in the preparation. Thus, a completely homogenous protein preparation will contain only one species of the particular polypeptide, e.g., a particular modification will be present to the same degree on all of that polypeptide in the preparation.

As used herein, the term "substituent group" refers to a chemical group attached on a molecule.

The term "fusion protein" is used herein in its conventional manner to refer to a protein that includes functional portions of at least two different proteins in a single amino acid sequence. In many cases, the fused proteins (e.g., two fused proteins) are joined by a linker sequence that is not necessary and/or not involved in the activities of the fused proteins. Such a linker can be "cleavable", meaning that the linker can be broken under conditions such that functional separate protein are produced from the fusion protein. In some cases, the linker can be completely or at least largely removed, e.g., by cleaving the linker at or near each end.

Reference to "Met" or "c-Met" herein refers to a transmembrane receptor binding hepatic growth factor (i.e., hepatocyte growth factor receptor). This receptor is referred to as c-Met, because it is the normal cellular protein that can malfunction to contribute to metastatic cancer. Specification of particular amino acid residues in c-Met utilize sequence NP_000236, encoded by nucleotide sequence NM_000245, at NCBI as the reference sequence.

Reference to "c-Abl" or "v-Abl" or "Abl" herein refers to *Homo sapiens* v-abl Abelson murine leukemia viral oncogene homolog 1 (ABL1). Specification of particular amino acid resudyes in Abl utilize sequence NP_005148, encoded by NM_005157 at NCBI.

In a related aspect, the invention provides a method for expressing in a cell an enzyme having reduced enzymatic modification by co-expressing a first recombinant enzyme with a second recombinant enzyme that removes a modification moiety from the first recombinant enzyme.

In particular embodiments, the first recombinant enzyme is self-modified; the first recombinant enzyme is expressed in a cell-based expression system and the first recombinant enzyme is modified by an endogenous enzyme produced by the cell; the first recombinant enzyme is selected from the group consisting of a kinase, a methylase, and an acetylase; the second recombinant enzyme is selected from the group consisting of a protein phosphatase, a protein demethylase, and a protein deacetylase (selected to reverse a modification on the first recombinant enzyme).

In another related aspect the invention concerns a method for expressing enzymatically active c-Met kinase domain by co-expressing a c-Met kinase domain with a phosphatase that removes phosphate groups from residues in the c-Met kinase domain, whereby phosphorylation of the c-Met tyrosine kinase domain is reduced as compared to expression of the c-Met kinase domain in the absence of expression of the phosphatase.

In particular embodiments, the c-Met kinase domain begins at one of residues 1049-1063 and ends at one of residues 1363-1408 of c-MET (these range specifications include both the ranges and each individual residue within the ranges including endpoints) where particular embodiments concern each combination of starting residue and ending residue in the specified ranges; the c-MET kinase domain consists essentially of residues 1056-1364; the c-Met kinase domain begins at one of residues 1049-1063 and ends at a residue in a range of 1365-1370, 1371-1375, 1376-1380, 1381-1385, 1386-1390, 1391-1395, 1396-1400, or 1401-1407 (these range specifications include both the ranges and each individual residue within the ranges including endpoints) where particular embodiments concern each combination of specific starting residue in the specified range and specific ending residue in one of the specified ranges.

Thus, in a related aspect, the invention provides polypeptide comprises, consists essentially of, or consists of a soluble c-Met kinase domain (e.g., human), for example, a human c-Met kinase domain. In particular embodiments, the c-Met kinase domain includes, consists essentially or, or consists of a polypeptide that begins at one of residues 1049-1063 and ends at one of residues 1363-1408 or at a residue in the range of 1365-1370, 1371-1375, 1376-1380, 1381-1385, 1386-1390, 1391-1395, 1396-1400, or 1401-1407 of human c-Met, where additional particular embodiments are as specified in the preceding method.

In particular embodiments, the c-Met kinase domain consists essentially of residues 1056-1364 of c-Met; the polypeptide is free of phosphate group modifications.

In another aspect, the invention provides a method for enhancing activity of a recombinant enzyme expressed in an expression system where the enzyme is inactive when modified with a substituent group, by co-expressing the enzyme with a second recombinant enzyme, where the second recombinant enzyme removes those substituent group.

In another aspect, the invention provides a crystal of a purified polypeptide consisting essentially of a protein modification enzyme catalytic domain, where the purified polypeptide self-modifies by addition of a modification moiety, and the purified polypeptide is free of that modification moiety.

In a related aspect, the invention provides a method for improving crystallization of a polypeptide subject to enzymatic modification by attachment of substituent groups when expressed in an expression system, by providing a purified polypeptide that has been co-expressed in the expression system with an enzyme that reduces the level of or eliminates modification with the substituent groups, whereby the homogeneity of the purified polypeptide is enhanced, and subjecting the purified polypeptide to crystallization conditions.

In another aspect, the invention provides a nucleic acid sequence encoding a first recombinant protein modification enzyme and a second recombinant protein modification enzyme that reverses the modification catalyzed by the first enzyme; and regulatory sequences adapted for expression of the first and second enzymes in an expression system. The respective coding sequences encoding the first and second enzymes may be in separate open reading frames, or in a single open reading frame encoding a fusion protein.

In a further aspect, the invention concerns a method for screening for enzyme inhibitors, by contacting a target enzyme free of a modification with a plurality of test compounds, where the target enzyme is activated by the presence of at least one such modification, and determining whether any of the test compounds bind to or inhibit the enzymatic activity of the target enzyme, where such binding or inhibition is indicative that the test compound is an inhibitor of the enzyme.

In particular embodiments, the target enzyme is a protein modification enzyme that is obtained by coexpressing the target enzyme with a second enzyme that reverses the protein self-modification catalyzed by the target enzyme; the target enzyme is a protein kinase, a methylase, or an acetylase; the target enzyme is obtained by coexpressing the target enzyme with a second enzyme that removes activating modification moieties on the target enzyme.

As used herein in connection with enzyme activity, the term "active" indicates that the polypeptide gives a signal that is at least 2-fold the background signal for the protein in a standard assay accepted by those of skill in the art for the relevant enzyme. For example, in protein kinase enzyme assays the minimal readout used to demonstrate activity is two-fold above the background readout created when the assay protocol is performed in the absence of the substrate ATP. In the case of a protein tyrosine kinase, antibodies are available (e.g., PY20, Perkin Elmer) that bind tightly to phospho-tyrosine residues that are the product of the enzyme reaction. Sensitive light signals of this antibody binding can be created using the AlphaScreen instrument (Perkin Elmer), from which the amount of activity of the kinase can be inferred. In the absence of the above assay, other standard protein kinase assay formats, such as the common ELISA format, also can be used to detect activity. In the ELISA format the substrate protein can be attached to the bottom of assay plates, and after the enzyme reaction is performed antibodies such as PY20 are bound to the phospho-tyrosine residues produced. Secondary antibodies that are attached to horseradish peroxidase and that bind the PY20 antibody can be used to produce a color reaction when reacted with specific substrates such as TMB (3,3',5,5'-tetramethylbenzidine). The amount of light absorbance caused by the bound horseradish peroxidase will relate to the amount of phospho-tyrosine residues present, from which the activity of the kinase can be inferred. Suitable assays are also known in the art for other enzymes, such as other protein kinases (e.g., serine/threonine and histidine kinases) and other enzymes. As the converse to the term "active", the term "inactive" indicates that the protein produces less than 2-fold signal over background in the relevant standard enzyme assay.

The term "activate", in connection with an enzyme, indicates that the enzyme has been changed in a manner resulting in significantly increased activity on a suitable substrate. In some cases, the activity of the non-activated form of the enzyme can be undetectable. In many cases, phosphorylation of a specific residue results in activation, e.g., activation of a kinase.

As used herein in connection with modulators of activity of a, the term "screening" refers to determining whether any of a plurality of test compounds have a desired biological effect, such as inhibition of an activity of a particular protein. The plurality of compounds, can for example, be at least 10, 100, 1000, 10,000, or more.

In yet another aspect, the invention concerns an expression vector that includes a first recombinant nucleic acid sequence encoding a first enzyme subject to enzymatic modification and a second recombinant nucleic acid sequence encoding a second enzyme that reverses that modification, where the first and second recombinant nucleic acid sequences are operatively linked with regulatory sequences such that the first and second recombinant nucleic acid sequences are expressed in a host cell.

A related aspect concerns a cell that includes a first recombinant nucleic acid sequence encoding a first enzyme subject to enzymatic modification, and a second recombinant nucleic acid sequence encoding a second enzyme that reverses that modification, where the first and second recombinant nucleic acid sequences are operatively linked with regulatory sequences such that the first and second recombinant nucleic acid sequences are expressed in the cell.

In certain embodiments of the present invention that involve co-expression of enzymes or constructs for carrying out such expression, expression is carried out in a cell-based expression system; the substituent group or modification moiety is a phosphate group, methyl group, or acetyl group; one or both of the first and second enzymes are provided as catalytic domains, such as kinase domain, phosphatase domain, methylase domain, de-methylase domain, acetylase domain, de-acetylase domain; a kinase domain is a c-Met kinase domain; an enzyme pair is a protein kinase and a protein phosphatase (e.g., a tyrosine protein kinase and a protein tyrosine phosphatase), a methylase and a de-methylase, or an acetylase and a de-acetylase; sequences encoding the first and second enzymes are configured such that the first and second enzymes will be or are encoded by a single mRNA, i.e., a bi-cistronic mRNA; sequences encoding the first and second enzymes are configured such that the first and second enzymes will be or are encoded by separate mRNAs; the first and second enzymes are expressed from a vector; the first enzyme is a protein modification enzyme; the first enzyme self-modifies when expressed as a recombinant protein in a bacterial cell, such as in $E.$ $coli$; the first enzyme consists essentially of a kinase domain and the second enzyme consists essentially of a phosphatase domain that reduces the level of phosphate group modification on the kinase domain; the first enzyme and the second enzyme are expressed at levels such that the ratio of first enzyme to second enzyme is in the range of 1:10 to 10:1, 1:5 to 5:1, 1:3 to 3:1, 1:2 to 2:1, or 1.5:1 to 1:1.5; sequences encoding the first and second enzymes are linked by additional coding sequences such that a single fusion protein having both enzymes is produced; first and second enzymes in a fusion protein are linked by additional coding sequences that function as a cleavable linker; the first and/or second enzymes are produced from genes stably integrated with the genes of the expression cell.

In another aspect, the invention concerns a method for identifying a soluble enzyme fragment, where the method involves expressing a set of fragments of the enzyme, thereby determining solubility and/or enzymatic activity of a plurality of fragments. One or more of the fragments are selected that provide soluble and/or active protein. If none of the fragments are soluble and/or active, a new set with different termini are constructed and tested until one or more fragments are identified that provide soluble and/or active enzyme. Generally, the process is carried out systematically such that available information about the enzyme is utilized in selecting termini for the fragments, such as exclusion of sequences that would result in surface hydrophobic residue patches, inclusion of sequences representing all or most of the catalytic domain.

In particular embodiments, at least 5, 7, 10, or more fragments of an enzyme that is insoluble when expressed in catalytic domain-length form are expressed and tested; each of the fragments has a C-terminal amino acid residue that is in the range of 100 residues outside to 20 residues inside the C-terminal catalytic domain boundary (or 100 residues outside to 10 residues inside, 70 residues outside to 10 residues inside, or 70 residues outside to 5 residues inside), and/or an N-terminal amino acid residue that is in the range of 100 residues outside to 20 residues inside the N-terminal catalytic domain boundary or 100 residues outside to 10 residues inside, 70 residues outside to 10 residues inside, or 70 residues outside to 5 residues inside); and analyzing relative levels of soluble and/or active polypeptide for each fragment in said set, thereby identifying soluble and/or active enzyme fragments, if any, in the set.

As used herein in connection with an enzyme, the term "set of fragments" refers to a plurality of portions of the amino acid sequence of the enzyme that include a sequence portion in common but have different termini at the C-terminus, N-terminus, or both.

In certain embodiments, the method is performed by analyzing a first plurality of fragments each having the same C-terminal amino acid residue and differing in their N-terminal amino acid residues for levels of soluble enzyme; selecting a fragment that provides soluble enzyme, where the fragment has a selected N-terminal amino acid residue; analyzing a second plurality of fragments that each has the selected N-terminal amino acid residue; and selecting a fragment that provides a high level of soluble enzyme relative to other fragments in said second plurality, The selected C-terminal amino acid residue in the first plurality of fragments can be selected to be at any of a variety of locations, for example, within 10, 20, 30, 40, or 50 residues of the C-terminal residue of the full-length enzyme polypeptide that includes that fragment and/or at least 10, 20, 30, 40, 50, 60, 80, or 100 residues outside the C-terminal catalytic domain boundary.

In particular embodiments, the method is carried out by analyzing a first plurality of fragments each comprising the same N-terminal amino acid residue and differing in their C-terminal amino acid residues for levels of soluble enzyme; selecting a fragment that provides soluble enzyme, wherein the fragment has a selected C-terminal amino acid residue; analyzing a second plurality of fragments that each has that selected C-terminal amino acid residue and different N-terminal amino acid residues; and selecting a fragment that provides a high level of soluble enzyme relative to other fragments in the second plurality. As indicated above for the C-terminus the N-terminus can be selected to be at a variety of different locations, for example, the N-terminal amino acid residue in the first plurality of fragments is within 10, 20, 30, 40, or 50 residues of the N-terminal residue of the full-length enzyme polypeptide that includes the fragment and/or the N-terminal amino acid residue in the first plurality of fragments is at least 50 residues outside the N-terminal catalytic domain boundary As used in connection with expression of complete or partial enzymes, the term "enzymatically active" indicates that the enzyme (e.g., catalytic domain) catalyzes the corresponding reaction on a substrate appropriate for that enzyme with an activity level that is detectable using an assay suitable for that enzyme. Conversely, the term "inactive" indicates that the enzyme catalyzes the corresponding reaction on a substrate appropriate for that enzyme at a level that is not detectable using the same assay.

In connection with expression of a recombinant polypeptide, the term "soluble" indicates that the polypeptide will remain in solution under particular conditions, i.e., does not precipitate out of solution or form large suspended clumps. In the context of the present invention, the term typically refers to solubility in an aqueous solution, e.g., one suitable for carrying out an enzymatic reaction with the polypeptide.

Additional embodiments will be apparent from the following Detailed Description and from the claims.

DETAILED DESCRIPTION OF THE PREFERRED EMBODIMENTS

Figure 1:
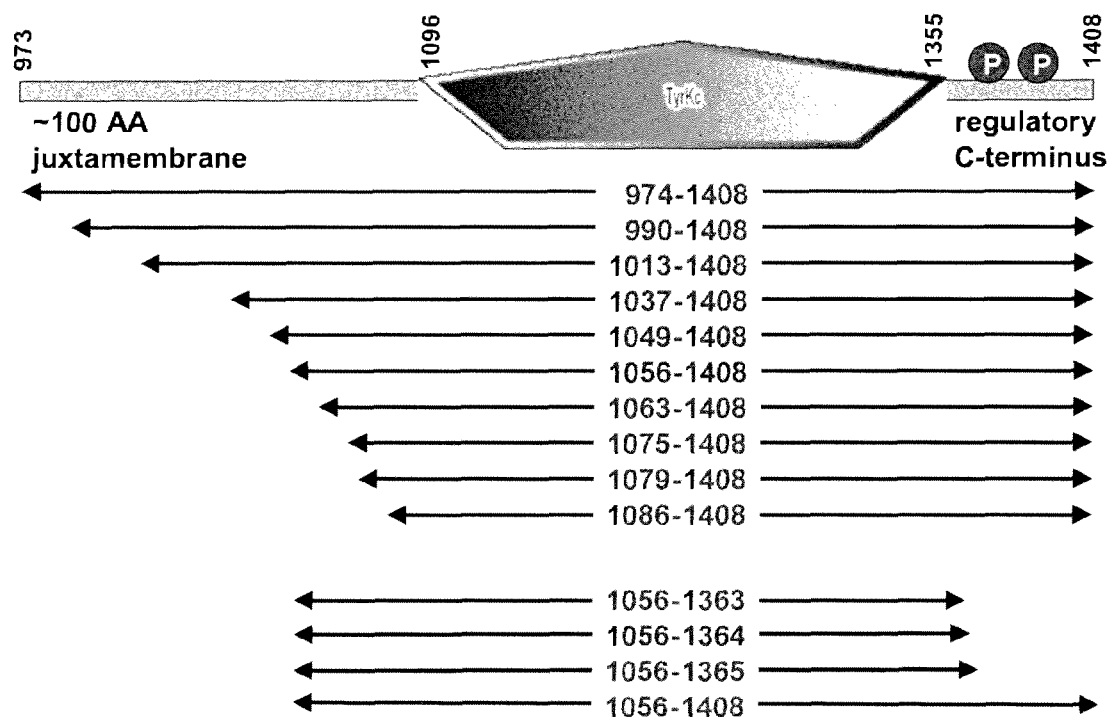
FIG. 1 illustrates the tyrosine kinase domain within human c-MET, and the various fragments constructed in an exemplary demonstration of identification of soluble catalytic domain from an insoluble parent molecule.

Genetic engineering methods can enable a person to produce amounts of gene-encoded proteins much higher than exist in normal organisms. When successful, such material can allow research and development related to these proteins that would be difficult or impossible using only material isolated from the normal organism. However, often the material produced through genetic engineering has inadequate yield, or fails to have properties expected of material from the normal organism, and such differences can limit their utility.

In the case of protein-modification enzymes, failure can result from a number of different causes. For example, the enzyme may alter the proteins of the expression host sufficiently to cause lower levels of enzyme production, such as through toxic effects on the host. When higher production levels are achieved, the enzyme may alter the structure of itself in an unnatural manner due to the high production levels, leading to alterations in normal properties or even complete loss of activity.

In addition to the difficulties involved in expression of recombinant enzymes in substantial quantities, some proteins, e.g., catalytic domains of enzymes, are difficult to obtain in active, soluble form. Examples include kinase domains of a number of membrane bound protein kinases, e.g., receptor tyrosine kinases.

The present invention provides methods for addressing both of the difficulties discussed above.

Co-expression of Enzymes Having Counteracting Activities

Methods described here involve producing the protein modification enzyme of interest coordinately with a second protein or agent having activity that can reverse or limit the unwanted actions. In a particular example, a protein tyrosine kinase (transferring phosphate from adenosine triphosphate to tyrosine groups on proteins) is simultaneously produced in bacteria with a protein tyrosine phosphatase (cleaves phosphate from phosphotyrosine groups on proteins). When produced singly, the protein tyrosine phosphatase becomes hyperphosphorylated, whereas when produced simultaneously with a protein tyrosine phosphatase it is essentially unphosphorylated.

The ability to produce the dephosphorylated kinase is advantageous for pharmaceutical research because this form allows biochemical assays to be performed that are impossible with the hyperphosphorylated form. For example, currently the sole kinase inhibitor approved for use in human therapy is 4-[(4-Methyl-1-piperazinyl)methyl]-N-[4-methyl-3-[[4-(3-pyridinyl)-2-pyrimidinyl]amino]-phenyl]benzamide methanesulfonate (Gleevec), which is known to target the dephosphorylated kinase specifically. In the biology of kinases, activity is often stimulated by residue-specific phosphorylation of the kinase by a second kinase or by residue-specific autophosphorylation, after which the kinase is in an activated state.

Thus, in at least some cases, the most effective kinase-inhibitory pharmaceuticals will act on the unphosphorylated kinase before it is activated, because the unactivated kinase may be more easily controlled if it is inhibited before it can be activated. In such cases, providing a source of unphosphorylated kinase is valuable for kinase pharmaceutical research and development. In situations where research and/or development with the phosphorylated, activated kinase is desired, having the unphosphorylated kinase is also valuable as a starting material for creating specifically phosphorylated protein under controlled conditions, without hyperphosphorylation at incorrect residues.

In addition to allowing use of non-activated enzyme in cases where a modification such as a phosphorylation activates the enzyme, reducing or eliminating a modification on a target enzyme can also be applied in other cases where the presence of a modification or modifications causes a difference in sensitivity of the target enzyme to modulator compounds, e.g., small molecules. For example, the presence of a modification(s) can alter the binding characteristics for binding of modulator in a binding site, e.g., at an active site. Such binding characteristics can occur by various mechanisms, e.g., by steric hindrance or blocking, preventing the modulator compound from binding, and/or by inducing comformational changes in the protein that alter the binding site in a manner that changes binding properties for modulators. Thus, in a variety of applications, it is beneficial to use protein for screening that is free from, or has a reduced level of modification, e.g. protein produced using co-expression as described herein. Such protein can be used directly, or can be subjected to controlled modification to introduce a desired level of modification or modification at specific sites. In many cases, the unmodified form is more sensitive to inhibitors.

Producing unmodified enzymes (e.g., dephosphorylated kinase) is also advantageous in the application of X-ray crystallography for pharmaceutical research. X-ray crystallography requires a source of target protein that can be purified to near-homogeneity so that the crystals obtained will yield high-resolution X-ray diffraction data. If a protein modification enzyme acts on itself, it will then exist in multiple forms (with different modification levels) that are difficult to purify to homogeneity. Producing unmodified enzyme, e.g., producing the unphosphorylated form of a protein kinase, as a homogeneous starting form is a distinct advantage. As with biochemical assays, the unmodified material can be used for structure analyses directly or after activating modification reactions have been performed under controlled conditions.

The method is not limited to kinases and phosphatases, but instead can be applied to the design of expression systems for numerous types of protein modification enzymes including, for example, without limitation:

a) protein kinase with protein phosphatase
b) protein methylase with protein demethylase
c) protein acetylase with protein deacetylase Although, in many cases, coexpression with the second enzyme is intended primarily to reverse or limit the activity of the first enzyme acting on itself, situations can also arise where the expression host or system has activities that modify the first enzyme. Such host modification can likewise be reversed by coexpression with the second enzyme. For example, an expression host system (e.g., a bacterial expression system) can modify the first enzyme in an unnatural manner, and those unnatural modifications can be removed with a co-expressed enzyme that removes the particular modification.

To achieve coordinate production of a protein modification enzyme with a reversing agent the two genes can be engineered together on a single DNA fragment, such as on a prokaryotic plasmid, either as two separate genes or such that a polycistronic mRNA is produced, or such that a fusion protein is produced. Alternatively the two genes can be engineered on two separate DNA fragments. The two genes may be differently localized or regulated in the cell, and introduced into the cell or organism at different times or by different means. The levels of protein accumulation and levels of activity of the protein modification enzyme and reversal agent encoded by the two genes may be varied separately to achieve different amounts of protein modification reversal. The reversing agent might be produced by a separate process and introduced into the cell or organism as a mRNA or protein rather than as a gene. Further, either or both of the protein modification enzyme and the reversing agent might be produced in an in vitro translation process.

After the production period, any of numerous schemes can be utilized for manipulating the protein modification enzyme to remove the reversing agent as needed, e.g., using a tag that allows the reversing agent to be preferentially bound to a solid phase medium and thereby separated from the protein modification enzyme.

Production of Soluble Enzyme Domains

As indicated above, when a person works with a protein or protein domain, usually an enzyme catalytic domain, in some cases difficulties are experienced in producing soluble active protein. For example, during either production in a cell or during purification, much (or even essentially all) of the recombinant protein agglomerates and/or precipitates, resulting in little or no soluble active recombinant protein.

It was found that often this problem can be solved by proper selection of the termini of the recombinant protein. In the case of an enzyme catalytic domain, it is common to attempt to use a protein fragment with termini at or close to the boundaries of the catalytic domain.

We discovered that the exact termini utilized can have a significant, even dramatic, effect on the level of production and/or activity of soluble recombinant protein. In some cases, varying a terminus by even one amino acid residue can significantly alter the amount of soluble and/or active protein obtained.

Thus, the present method involves systematic testing of multiple fragments to identify suitable termini for a soluble and/or active protein. This process can be performed in various ways, but generally involves testing a plurality of fragments while co-varying the termini in small increments around the N- and C-termini of the domain of interest (or other portion of interest of the protein). One or more specific fragments are selected that give levels of soluble and/or active protein that are better than others in the set. One or more of these fragments then serves as the basis for selecting and testing additional fragment that have termini close to the termini of the initially selected fragment. Such selection and testing can be performed multiple times as needed, e.g., using small variations. If needed to obtain acceptable production, one or both termini can be varied to produce a set of fragments that differ by as little as 1 residue at a terminus (or both termini).

In practice, it is often advantageous to vary only one terminus at a time. In such an implementation, one terminus is fixed (e.g., at a domain boundary or at the end of the native protein) while the other terminus is varied to produce a set of fragments that vary in length by small increments. This initial set is tested. If a fragment or fragment provides better production than others, such fragment or fragments can be selected as the basis for a second round of construction and selection. While the same terminus can be varied on a finer scale, in many cases, it is more efficient to vary the other (previously invariant) terminus, test the resulting fragments, and select a fragment that gives better production. This process can be repeated, varying one or both termini to identify a fragment that provides acceptable production.

The selection of initial termini can depend on where in the native protein the domain (or other portion of interest) is located. For example, if the domain is located near one end of the native protein, it can be advantageous to initially fix one terminus at or near the end of the native protein, and vary the other terminus. If the domain is located further away from the native terminus, it can be advantageous to utilize an initial terminus outside the domain on one end, and vary the other terminus near the other domain boundary.

In many cases, a terminus will be varied within the range of 100 aa outside to 20 aa inside a domain boundary (e.g., catalytic domain boundary). In other embodiments, one or both termini can be varied in the range of 100 aa outside to 10 aa inside, 50 outside to 20 inside, 50 outside to 10 inside, 100 outside to 5 inside, 50 outside to 5 inside, 30 outside to 20 inside, 30 outside to 10 inside, 30 outside to 5 inside, 100 outside to 0 inside, 50 outside to 0 inside, 30 outside to 0 inside a domain boundary, as well as other ranges.

Nucleic acid sequences encoding protein or polypeptides for use in the present invention can be obtained from conventional sources, e.g., from sequence depositories, synthesized from sequence information, subcloned from a clone library, or cloned from a source organism.

Genetic constructs useful in the present invention can be constructed using conventional cloning methods, allowing cloning, construction of recombinant constructs, production and purification of recombinant protein, introduction of constructs into other organisms, and other molecular biological manipulations of specific protein coding sequences are readily performed.

Techniques for the manipulation of nucleic acids, such as, e.g., subcloning, labeling probes (e.g., random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (11997); Laboratory Techniques in Biochemistry and Molecular Biology: Hybridization With Nucleic Acid Probes, Part I. Theory and Nucleic Acid Preparation, Tijssen, ed. Elsevier, N.Y. (1993), as well as numerous other sources.

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., *Nucleic Acids Res.* 2001 Jun. 1; 29(11):E54-E54; Hafner et al., *Biotechniques* 2001 April; 30(4):852-6, 858, 860 passim; Zhong et al., *Biotechniques* 2001 April; 30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in. e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Depending on the host vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the desired DNA, SV40-, BPV- and EBV-based vectors may be used with an appropriate selectable marker.

Thus, the nucleic acids of the invention can be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

A variety of host-expression vector systems may be utilized to express the desired coding sequence(s). These include but are not limited to microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The expression elements of these systems vary in their strength and specificities.

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin vector is a derivative of the pET-24 vector (Novagen) designed to utilize the T7 RNA polymerase for producing mRNA in strains of E. coli that are engineered to produce that polymerase.

A DNA fragment encoding the human PTP1b phosphatase domain extending from PTP1b residue Met 1 through to residue Gly 283 was engineered using PCR. The template for the PCR reaction was a previously-engineered human PTP1b cDNA derived from a purchased total human brain cDNA library (Invitrogen). Custom oligonucleotide primers (Invitrogen) were designed to create a ribosome binding site and a SalI site (GTCGAC) flanking the 5'-side (PTP-SAL), and an EcoRI site (GAATTC) flanking the 3'-side (PTP-RI) of the encoded phosphatase domain. The PTP-SAL oligonucleotide primes the coding strand of PTP1b and the PTP-RI PCR oligonucleotide primes the non-coding strand of PTP1b. These primer sequences are shown below:

```
DNA oligonucleotide primer - Coding strand
PTP-SAL  5'-CTGCGAA GTCGAC GAAGGAGATATATCC ATGGAGATGGAAAAGGAGTTCG    (SEQ ID NO: 1)

DNA oligonucleotide primer - Noncoding strand
PTP-RI   5'-CTGCGAAGAATTC TCACCCCATGATGAATTTGGCACCT                  (SEQ ID NO: 2)
``` chromatography. Protein refolding steps can be used, as necessary, in completing configuration of the polypeptide. If desired, high performance liquid chromatography (HPLC) can be employed for final purification steps.

In addition to bacterial culture systems, various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Exemplary embodiments of the invention are shown by the non-limiting examples described herein.

EXAMPLES

Example 1

Engineering a Bicistronic Vector Encoding Both Abl Kinase Domain and PTP1b Phosphatase Domain The bicistronic vector engineering used, as a starting material, a previously-engineered vector that encodes human Abl (Abelson tyrosine kinase) kinase domain extending from Abl residue Gly 227 through to residue Val 515, termed pET-SPEC BI-PTP Abl G227-V515-X. The section of this plasmid that encodes Abl kinase and PTP1b domains on a bicistronic mRNA transcript is shown in Table 2. The remainder of the After performing a standard PCR reaction, the product obtained was cut with the restriction enzymes, SalI and EcoRI (New England Biolabs), and purified by agarose gel electrophoresis. The pET-SPEC Abl G227-V515-X vector contains unique SalI and EcoRI restriction sites immediately downstream of the Abl coding region. The pET-SPEC Abl G227-V515-X vector was cut with SalI and EcoRI, and purified by agarose gel electrophoresis. The PTP1b DNA and the pET-SPEC Abl G227-V515-X vector DNA were ligated together using T4 DNA ligase (Invitrogen) to create a circular plasmid suitable for the bicistronic expression of the Abl kinase domain and the PTP1b phosphatase domain in E. coli.

The plasmid vector was introduced into E. coli, amplified during the E. coli growth, and extracted for analysis. Relevant DNA sequences were determined (Davis Sequencing). The relevant DNA sequence for this vector, pET-SPEC BI-PTP Abl G227-V515-X, with the encoded amino acid sequences of the Abl and PTP proteins, shown in Table 2. The DNA sequence that matches the mRNA transcript is shown above the amino acid sequences that are encoded by this mRNA. The bicistronic mRNA encodes first the Abl kinase followed by the PTP1b phosphatase domain. Abl kinase domain extends from residue G227 through V515, and is preceded by an N-terminal His tag (MGHHHHHH). (SEQ ID NO: 3) The PTP1b phosphatase domain extends from residue M1 through G283. Both the Abl and PTP1b coding regions are preceded by ribosome binding sites (AAGGAG) in the mRNA.

Example 2

Expression in E. coli of His-tagged Abl Protein from pET-SPEC BI-PTP Abl G227-V515-X To obtain protein expression of dephosphorylated Abl, the pET-SPEC BI-PTP Abl G227-V515-X DNA was transfected into the E. coli strain BL21-CodonPlus(DE3)-RIL (Stratagene) using standard methods, with dual antibiotic selection of kanamycin and chloramphenicol. E. coli harboring the plasmid were grown in liquid culture at 37° C. with shaking to an OD600=1, at which point the culture temperature was reduced to 15° C., and the 0.5 mM IPTG inducing agent was added. The culture was then shaken for 18 hrs at 15° C., at which point the *E. coli* was concentrated by centrifugation.

The *E. coli* pellet, 0.5 g, was suspended in 10 ml buffer (50 mM Tris pH 7.5, 250 mM NaCl, 0.1% Triton-X-100, 0.02% monothioglycerol, 20 uM phenylmethylsulfonyl chloride). Extraction was initiated by addition of lysozyme (Sigma) to 200 ug per ml, incubation on ice for 15 min, and sonication for 1 min. Solution was centrifuged 30 min at 17000 RPM in SA600 rotor (Sorvall) at 4 C. The supernatant was recovered, and Histidine-tagged Abl protein was purified using metal affinity chromatography by mixing supernatant with 600 ul 50% slurry of buffer-washed Talon beads (Clontech) for 1 hr at 4° C., in the presence of 10 mM imidazole. The beads are washed 3 times with 10 mls of buffer (50 mM Tris pH 7.5, 100 mM NaCl, 0.02% monothioglycerol, 20 uM phenylmethylsulfonyl chloride and 10% glycerol) with centrifugation at 4000 RPM between washes. Abl protein was eluted from pelleted beads using 1 ml buffer (50 mM Tris pH 7.7, 100 mM NaCl, 10% glycerol, 200 mM imidazole). Eluted proteins were concentrated by centrifugation in Centriprep concentrators (Millipore).

The concentrated protein was buffer-exchanged by gel filtration chromatography using P-10 columns (Pharmacia), equilibrated in buffer (50 mM Tris pH 7.7, 100 mM NaCl, and 10% glycerol). Eluted protein was flash-frozen in liquid nitrogen and stored at −80° C. With this purification protocol His-tagged Abl protein at >80% purity is achieved. The coexpressed PTP is not present, as expected because it lacked the Histidine tag and should therefore not bind the Talon beads.

Example 3

Determination that Abl Co-expressed with Phosphatase is not Phosphorylated

Abl proteins expressed either with or without PTP coexpression were evaluated for state of phosphorylation detectable with an antibody that specifically binds phospho-Tyr (PY20 mouse monoclonal IgG$_{2b}$, SantaCruz Biotechnology). Samples of Abl made from each expression vector were separated by size using SDS-PAGE, then transferred by electroblotting onto Imobilon-P membrane (Millipore) in transfer buffer (39 mM Glycine, 48 mM Tris HCl, 20% MeOH, 0.0375% SDS). The membrane was stained with coomassie to visualize the Abl proteins. Before exposure to antiserum the membrane was exposed to phosphate-buffered saline containing 0.1% Tween detergent and 5% bovine serum albumin to reduce background antibody binding. The paper was then exposed for 2 hr at room temperature to 1:1000 dilution of PY20 antibody prepared in the same buffer. After washing, membrane was exposed for 2 hr at room temperature to 1:5000 dilution goat anti-mouse IgG (H+L) coupled to horseradish peroxidase (Pierce). Membrane is washed three times as before. Visualization of binding was made using chemical luminescence methodology with ECL detection reagent (Amersham Biosciences) according to manufacturer's protocol. Inspection of the finished blot indicated that the Abl coexpressed with PTP1B has little or no phosphorylation above background, whereas Abl coexpressed alone is highly phosphorylated.

Example 4

Determination of Activities of Unphosphorylated Abl and Hyperphosphorylated Abl

The activity of the Abl was assayed using AlphaScreen Phosphotyrosine (PY20) Assay Kits (PerkinElmer). 20 ng of Abl protein was mixed with 5 uM ATP (Sigma), 50 pmol BIO-E4Y3 peptide (New England Biolabs), 20 nl Streptavidin donor beads, and 20 nl Anti-phosphotyrosine (PY20) acceptor beads in 20 ul reaction buffer (50 mM Hepes pH 7.1, 1 mM MgCl$_2$, 0.1% IGPAL, 0.005% BSA), and incubation performed at 37° C. for 2 hours before reading in a Fusion Universal Microplate Analyzer (Perkin Elmer). For inhibitor studies, 1 ul of drug was added to the empty assay plate first.

The Abl coexpressed with PTP was compared to Abl expressed alone for sensitivity to the inhibitor, Gleevec. Various concentrations were tested for inhibition of the kinase signal seen in the AlphaScreen assay. Gleevec could inhibit completely both types of Abl, but 47 nM Gleevec was required to achieve 50% inhibition of the Abl coexpressed with PTP, whereas 5 uM Gleevec achieved 50% inhibition of the Abl expressed alone, indicating that 100-fold higher Gleevec was required to inhibit the phosphorylated form.

Example 5

Engineering a Family of Bicistronic Vectors for Coexpression of Either *Yersinia tyrosine* Phosphatase, VHR Phosphatase, or Lambda Phosphatase Phosphatases vary in their substrate specificities and activities. PTP1b is restricted to phosphotyrosine as substrate, whereas other phosphatases act on other phosphorylated residues, e.g., serine/threonine or histidine. Thus, other selections of phosphatases can be used in particular applications. To expand the choices of phosphatase for coexpression, vectors were engineered having YOP tyrosine phosphatase, VHR phosphatase, or lambda phosphatase. Sequences for other types of phosphatases (as well as other enzymes) can be obtained from publicly available sequence databases, such as GenBank, SwissProt, and the like. For example, the amino acid sequence and accession number for lambda phosphatase is provided in Table 4.

For engineering of the YOP and lambda vectors, PCR cloning methods analogous to the engineering of the bicistronic vector for coexpression with PTP1B were used. For the VHR vector, a complete gene synthesis of the VHR coding region was performed using synthetic oligo primers. Each vector has NdeI and SalI sites available for accepting DNA fragments encoding targets of interest as a Histidine-tagged protein on a single mRNA also encoding the non-tagged phosphatase. We refer to these vectors as pET-N6 BI-YOP, pET-N6 BI-VHR, and pET-N6 BI-LAM.

Example 6

Engineering a Soluble, Enzymatically Active c-Met Kinase Domain by Systematically Varying the Choice of Encoded N-terminal and C-terminal Kinase Domain Boundaries The MET kinase domain is the intracellular part of a transmembrane receptor binding hepatic growth factor (i.e., hepatocyte growth factor receptor). This receptor is referred to as c-Met, because it is the normal cellular protein that can malfunction to contribute to metastatic cancer. Although of interest for 20 years as a target for anti-cancer drug development, it has never successfully been expressed as a soluble protein in *E. coli*. We identified boundaries of the MET kinase domain that yield soluble active protein when engineered for expression in bacteria.

The first step of a two-step approach was to systematically test several different upstream boundaries in conjunction with the natural C-terminus (residue 1408), and to examine the *E. coli*-expressed products for the comparative levels of soluble MET kinase protein and comparative levels of insoluble MET kinase protein produced. Of 10 N-terminal boundaries tested, residue Gly 1056 was chosen because it showed the most (albeit weak) soluble expression with the least (albeit large) amount of insoluble expression. In the second step residue Gly 1056 was kept constant while four alternative C-termini were compared. With Gly 1056 as the N-terminal boundary and Gly 1364 as the C-terminal boundary, soluble active MET kinase protein was generated at levels useful for biochemical assays and crystallization.

To produce the various kinase domains described above, the complete intracellular domain of c-MET was cloned using a standard PCR reaction using human brain cDNA (Invitrogen) as a template mixture and primers Met 950 and Ser-1408 (see table below). This complete domain was cloned into a His-tagged vector, pET-N6 that is a derivative of pET24 (Novagen). The pET-N6 vector is modified to encode a His tag (MGHHHHHHM) (SEQ ID NO: 4) that is fused to the N-terminus of coding sequences engineered after it, and also includes a polylinker with NdeI, NotI, SalI, and EcoRI sites. Standard PCR reactions were used to engineer the various lengths of MET, using appropriate combinations of two primers from the table below.

These were cloned into the pET-N6 vector and the pET-N6 BI-PTP bicistronic vector for MET expression alone, or with PTP1B. When expressed alone the MET was phosphorylated and when coexpressed with PTP1B the MET was unphosphorylated, as determined using methods as described for the Abl kinase domain. Both the phosphorylated and unphosphorylated forms of MET kinase had kinase activity in the same assay format as described for Abl kinase.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to the particular enzymes or enzyme pairs utilized. Thus, such additional embodiments are within the scope of the present invention and the following claims.

The invention illustratively described herein suitably may be practiced in the absence of any element or elements, limitation or limitations which is not specifically disclosed herein.

TABLE 1

| Starting amino acid residue | | SEQ ID NO |
|---|---|---|
| DNA oligonucleotide primer - Coding strand | | |
| Met 950 | 5'-GAATTAGTT CATATG GATGCAAGAGTACACACTCCTCA | 5 |
| Lys 974 | 5'-TTTCCTG CATATG AAAAAGAGAAAGCAAATTAAAGATCT | 6 |
| Met 1013 | 5'-AACTACA CATATG GTTTCAAAATGAATCTGTAGACTAC | 7 |
| Gly 1037 | 5'-TTCATCT CATATG GGTTCATGCCGACAAGTGCAG | 8 |
| Met 1049 | 5'-TCTGACA CATATG TCCCCCATCCTAACTAGTGG | 9 |
| Gly 1056 | 5'-CATCCTA CATATG GGGGACTCTGATATATCCAGTC | 10 |
| Ala 1075 | 5'-GCAGCTA CATATG GCTCTAAATCCAGAGCTGGTCAT | 11 |
| Glu 1079 | 5'-TGCTCTA CATATG GAGCTGGTCCAGGCAGTGCA | 12 |
| Ala 1083 | 5'-GCAGCTA CATATG GGAAGAGGGCATTTTGGTTGTGT | 13 |
| Pro 1063 | 5'-GCAGCTA CATATG CCATTACTGCAAAATACTGTCCAC | 14 |
| DNA oligonucleotide primer - Noncoding strand | | |
| Ile 1363 | 5'-GACAA GTCGAC TA AATGAAAGTAGAGAAGATCGCTG | 15 |
| Gly 1364 | 5'-CTAGCAG GTCGAC TA CCCAATGAAAGTAGAGAAGATCGC | 16 |
| Glu 1365 | 5'-CTAGCAG GTCGAC TA CTCCCCAATGAAAGTAGAGAAGAT | 17 |
| Ser 1408 | 5'-AGGATCC GTCGAC TA TGATGTCTCCCAGAAGGAG | 18 |

Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

TABLE 2 pET-SPEC BI-PTP Abl G227-V515-X (SEQ ID NO: 19)
(Encoded amino acid sequences are disclosed as SEQ ID NOS 23-24)

```
TAATACGACTCACTATAGGGGAATTGTGAGCGGATAACAATTCCCCTCTAGAAATAATTT

TGTTTAACTTTAAGAAGGAGATATACCATGGGTCACCACCATCACCACCACGGTGTGTCC
                                  M   G   H   H   H   H   H   G   V   S

CCCAACTACGACAAGTGGGAGATGGAACGCACGGACATCACCATGAAGCACAAGCTGGGC
 P   N   Y   D   K   W   E   M   E   R   T   D   I   T   M   K   H   K   L   G

GGGGGCCAGTACGGGGAGGTGTACGAGGGCGTGTGGAAGAAATACAGCCTGACGGTGGCC
 G   G   Q   Y   G   E   V   Y   E   G   V   M   K   K   Y   S   L   T   V   A

GTGAAGACCTTGAAGGAGGACACCATGGAGGTGGAAGAGTTCTTGAAAGAAGCTGCAGTC
 V   K   T   L   K   E   D   T   M   E   V   E   E   F   L   K   E   A   A   V

ATGAAAGAGATCAAACACCCTAACCTGGTGCAGCTCCTTGGGGTCTGCACCCGGGAGCCC
 M   K   E   I   K   H   P   N   L   V   Q   L   L   G   V   C   T   R   E   P

CCGTTCTATATCATCACTGAGTTCATGACCTACGGGAACCTCCTGGACTACCTGAGGGAG
 P   F   Y   I   I   T   E   F   M   T   Y   G   N   L   L   D   Y   L   R   E

TGCAACCGGCAGGAGGTGAACGCCGTGGTGCTGCTGTACATGGCCACTCAGATCTCGTCA
 C   N   R   Q   E   V   N   A   V   V   L   L   Y   M   A   T   Q   I   S   S

GCCATGGAGTACCTGGAGAAGAAAAACTTCATCCACAGAGATCTTGCTGCCCGAAACTGC
 A   M   E   Y   L   E   K   K   N   F   I   H   R   D   L   A   A   R   N   C

CTGGTAGGGGAGAACCACTTGGTGAAGGTAGCTGATTTTGGCCTGAGCAGGTTGATGACA
 L   V   G   E   N   H   L   V   K   V   A   D   F   G   L   S   R   L   M   T

GGGGACACCTACACAGCCCATGCTGGAGCCAAGTTCCCCATCAAATGGACTGCACCCGAG
 G   D   T   Y   T   A   H   A   G   A   K   F   P   I   K   W   T   A   P   E

AGCCTGGCCTACAACAAGTTCTCCATCAAGTCCGACGTCTGGGCATTTGGAGTATTGCTT
 S   L   A   Y   N   K   F   S   I   K   S   D   V   W   A   F   G   V   L   L

TGGGAAATTGCTACCTATGGCATGTCCCCTTACCCGGGAATTGACCTGTCCCAGGTGTAT
 W   E   I   A   T   Y   G   M   S   P   Y   P   G   I   D   L   S   Q   V   Y

GAGCTGCTAGAGAAGGACTACCGCATGGAGCGCCCAGAAGGCTGCCCAGAGAAGGTCTAT
 E   L   L   E   K   D   Y   R   M   E   R   P   E   G   C   P   E   K   V   Y

GAACTCATGCGAGCATGTTGGCAGTGGAATCCCTCTGACCGGCCCTCCTTTGCTGAAATC
 E   L   M   R   A   C   W   Q   W   N   P   S   D   R   P   S   F   A   E   I

CACCAAGCCTTTGAAACAATGTTCCAGGAATCCAGTATCTCAGACGAAGTGGAAAAGGAG
 H   Q   A   F   E   T   M   F   Q   E   S   S   I   S   D   E   V   E   K   E

CTGGGGAAACAAGGCGTCTGAGTCGACGAAGGAGATATATCCATGGAGATGGAAAAGGAG
 L   G   K   Q   G   V   -                           M   E   M   E   K   E

TTCGAGCAGATCGACAAGTCCGGGAGCTGGGCGGCCATTTACCAGGATATCCGACATGAA
 F   E   Q   I   D   K   S   G   S   W   A   A   I   Y   Q   D   I   R   H   E
```

TABLE 2-continued pET-SPEC BI-PTP Abl G227-V515-X (SEQ ID NO: 19)
(Encoded amino acid sequences are disclosed as SEQ ID NOS 23-24)

```
GCCAGTGACTTCCCATGTAGAGTGGCCAAGCTTCCTAAGAACAAAAACCGAAATAGGTAC
 A   S   D   F   P   C   R   V   A   K   L   P   K   N   K   N   R   N   R   Y

AGAGACGTCAGTCCCTTTGACCATAGTCGGATTAAACTACATCAAGAAGATAATGACTAT
 R   D   V   S   P   F   D   H   S   R   I   K   L   H   Q   E   D   N   D   Y

ATCAACGCTAGTTTGATAAAAATGGAAGAAGCCCAAAGGAGTTACATTCTTACCCAGGGC
 I   N   A   S   L   I   K   M   E   E   A   Q   R   S   Y   I   L   T   Q   G

CCTTTGCCTAACACATGCGGTCACTTTTGGGAGATGGTGTGGGAGCAGAAAAGCAGGGGT
 P   L   P   N   T   C   G   H   F   W   E   M   V   W   E   Q   K   S   R   G

GTCGTCATGCTCAACAGAGTGATGGAGAAAGGTTCGTTAAAATGCGCACAATACTGGCCA
 V   V   M   L   N   R   V   M   E   K   G   S   L   K   C   A   Q   Y   W   P

CAAAAAGAAGAAAAAGAGATGATCTTTGAAGACACAAATTTGAAATTAACATTGATCTCT
 Q   K   E   E   K   E   M   I   F   E   D   T   N   L   K   L   T   L   I   S

GAAGATATCAAGTCATATTATACAGTGCGACAGCTAGAATTGGAAAACCTTACAACCCAA
 E   D   I   K   S   Y   Y   T   V   R   Q   L   E   L   E   N   L   T   T   Q

GAAACTCGAGAGATCTTACATTTCCACTATACCACATGGCCTGACTTTGGAGTCCCTGAA
 E   T   R   E   I   L   H   F   H   Y   T   T   W   P   D   F   G   V   P   E

TCACCAGCCTCATTCTTGAACTTTCTTTTCAAAGTCCGAGAGTCAGGGTCACTCAGCCCG
 S   P   A   S   F   L   N   F   L   F   K   V   R   E   S   G   S   L   S   P

GAGCACGGGCCCGTTGTGGTGCACTGCAGTGCAGGCATCGGCAGGTCTGGAACCTTCTGT
 E   H   G   P   V   V   V   H   C   S   A   G   I   G   R   S   G   T   F   C

CTGGCTGATACCTGCCTCTTGCTGATGGACAAGAGGAAAGACCCTTCTTCCGTTGATATC
 L   A   D   T   C   L   L   L   M   D   K   R   K   D   P   S   S   V   D   I

AAGAAAGTGCTGTTAGAAATGAGGAAGTTTCGGATGGGGCTGATCCAGACAGCCGACCAG
 K   K   V   L   L   E   M   R   K   F   R   M   G   L   I   Q   T   A   D   Q

CTGCGCTTCTCCTACGTGGCTGTGATCGAAGGTGCCAAATTCATCATGGGGTGAGAATTC
 L   R   F   S   Y   L   A   V   I   E   G   A   K   F   I   M   G   -

GSGGCCAGCAGGGCCACCGCTGAGCAATAACTAGCATAACCCCTTGGGGCCTCTAAACGG

TCTTGAGGGGTTTTTG
```

TABLE 3

*Homo sapiens* protein tyrosine phosphatase, non-receptor type 1 (PTPN1), mRNA 3318 bp linear.

ACCESSION NUMBER NM_002827

REFERENCE 1 (bases 1 to 3318); Sun et al. (2003) J. Biol. Chem. 278: 12406-12414, Crystal structure of PTO1B complexed with a potent and selective bidentate inhibitor REFERENCE 2 (bases 1 to 3318); Boute et al. (2003) EMBO Rep. 4: 313-319.

REFERENCE 17 (bases 1 to 3318); Charbonneau et al. (1989) Human placenta protein-tyrosine-phosphatase: amino acid sequence and relationship to a family of receptor-like proteins, Proc. Natl. Acad. Sci. USA 86: 5252-5256. The protein encoded by this gene is the founding member of the protein tyrosine phosphatase (PTP) family, which was isolated and identified based on its enzymatic activity and amino acid sequence. PTPs catalyze the hydrolysis of the phosphate monoesters specifically on tyrosine residues. Members of the PTP family share a highly conserved catalytic motif, which is essential for the catalytic activity. PTPs are known to be signaling molecules that regulate a variety of cellular processes including cell growth, differentiation, mitotic cycle, and oncogenic transformation. This PTP has been shown to act as a negative regulator of insulin signaling by dephosphorylating the phosphotryosine residues of insulin receptor kinase. This PTP was also reported to dephosphorylate epidermal growth TABLE 3-continued factor receptor kinase, as well as JAK2 and TYK2 kinases, which implicated the role of this PTP in cell growth control, and cell response to interferon stimulation.

(SEQ ID NO: 20)
translation = "MEMEKEFEQIDKSCSWAAIYQDIRHEASDFPCRVAKLPKNKNRN
RYRDVSPFDHSRIKLHQEDNDYINASLIKMEEAQRSYILTQGPLPNTCGHFWEMVWEQ
KSRGVVMLNRVMEKGSLKCAQYWPQKEEKEMIFEDTNLKLTLISEDIKSYYTVRQLEL
ENLTTQETREILHFHYTTWPDFGVPESPASFLNFLFKVRESGSLSPEHGPVVVHCSAG
IGRSGTFCLADTCLLLMDKRKDPSSVDIKKVLLEMRKFRMGLIQTADQLRFSYLAVIE
GAKFIMCDSSVQDQWKELSHEDLEPPPEHIPPPPRPPKRILEPHNGKCREFFPNHQWV
KEETQEDKDCPIKEEKGSPLNAAPYGIESMSQDTEVRSRVVGGSLRGAQAASPAKGEP
SLPEKDEDHALSYWKPFLVNMCVATVLTAGAYLCYRFLFNSNT"

base pairs 181 . . . 1011 encode Protein tyrosine phosphatase catalytic domain (SEQ ID NO: 21)
```
   1 gtgatgcgta gttccggctg ccggttgaca tgaagaagca gcagcggcta gggcggcggt
  61 agctgcaggg gtcggggatt gcagcgggcc tcggggctaa gagcgcgacg cggcctagag
 121 cggcagacgg cgcagtgggc cgagaaggag gcgcagcagc cgccctggcc cgtcatggag
 181 atggaaaagg agttcgagca gatcgacaag tccgggagct gggcggccat ttaccaggat
 241 atccgacatg aagccagtga cttcccatgt gagtggcca agctccctaa gaacaaaaac
 301 cgaaataggt acagagacgt cagtcccttt gaccatagtc ggattaaatt acatcaagaa
 361 gataatgact atatcaacgc tagtttgata aaaatggaag aagcccaaag gagttacatt
 421 cttacccagg gcccttttgcc taacacatgc ggtcactttt gggagatggt gtgggagcag
 481 aaaagcaggg gtgtcgtcat gctcaacaga gtgatggaga aaggttcgtt aaaatgcgca
 541 caatactggc cacaaaaaga gaaaaagag atgatctttg aagacacaaa tttgaaatta
 601 acattgatct ctgaagatat caagtcatat tatacagtgc gacagctaga attggaaaac
 661 cttacaaccc aagaaactcg agagatctta catttccact ataccacatg gcctgacttt
 721 ggagtccctg aatcaccagc ctcattcttg aactttcttt tcaaagtccg agagtcaggg
 781 tcactcagcc cggagcacgg gccgttgtg gtgcactgca gtgcaggcat cggcaggtct
 841 ggaaccttct gtctggctga tacctgcctc ttgctgatgg acaagaggaa agacccttct
 901 tccgttgata tcaagaaagt gctgttagaa atgaggaagt ttcggatggg gctgatccag
 961 acagccgacc agctgcgctt ctcctacctg gctgtgatcg aaggtgccaa attcatcatg
1021 ggggactctt ccgtgcagga tcagtggaag gagctttccc acgaggacct ggagccccca
1081 cccgagcata tccccccacc tccccggcca cccaaacgaa tcctggagcc acacaatggg
1141 aaatgcaggg agttcttccc aaatcaccag tgggtgaagg aagagaccca ggaggataaa
1201 gactgcccca tcaaggaaga aaaggaagc cccttaaatg ccgcacccta cggcatcgaa
1261 agcatgagtc aagacactga agttagaagt cgggtcgtgg ggggaagtct tcgaggtgcc
1321 caggctgcct cccagccaa aggggagccg tcactgcccg agaaggacga ggaccatgca
1381 ctgagttact ggaagccctt cctggtcaac atgtgcgtgg ctacggtcct cacggccggc
1441 gcttacctct gctacaggtt cctgttcaac agcaacacat agcctgaccc tcctccactc
1501 cacctccacc cactgtccgc ctctgcccgc agagcccacg cccgactagc aggcatgccg
1561 cggtaggtaa gggccgccgg accgcgtaga gagccgggcc ccggacggac gttggttctg
1621 cactaaaacc catcttcccc ggatgtgtgt ctcacccctc atcctttac ttttgcccc
1681 ttccactttg agtaccaaat ccacaagcca tttttgagg agagtgaaag agagtaccat
1741 gctggcggcg cagagggaag gggcctacac ccgtctgggg ctcgccccca cccagggctc
1801 cctcctggag catcccaggc gggcggcacg ccaacagccc cccccttgaa tctgcaggga
```

TABLE 3-continued

```
1861 gcaactctcc actccatatt tatttaaaca attttttccc caaaggcatc catagtgcac
1921 tagcattttc ttgaaccaat aatgtattaa aattttttga tgtcagcctt gcatcaaggg
1981 ctttatcaaa aagtacaata ataaatcctc aggtagtact gggaatggaa ggctttgcca
2041 tgggcctgct gcgtcagacc agtactggga aggaggacgg ttgtaagcag ttgttattta
2101 gtgatattgt gggtaacgtg agaagataga acaatgctat aatatataat gaacacgtgg
2161 gtatttaata agaaacatga tgtgagatta ctttgtcccg cttattctcc tcctgttat
2221 ctgctagatc tagttctcaa tcactgctcc cccgtgtgta ttagaatgca tgtaaggtct
2281 tcttgtgtcc tgatgaaaaa tatgtgcttg aaatgagaaa ctttgatctc tgcttactaa
2341 tgtgccccat gtccaagtcc aacctgcctg tgcatgacct gatcattaca tggctgtggt
2401 tcctaagcct gttgctgaag tcattgtcgc tcagcaatag ggtgcagttt ccaggaata
2461 ggcatttgcc taattcctgg catgacactc tagtgacttc ctggtgaggc ccagcctgtc
2521 ctggtacagc agggtcttgc tgtaactcag acattccaag ggtatgggaa gccatattca
2581 cacctcacgc tctggacatg atttagggaa gcagggacac cccccgcccc ccacctttgg
2641 gatcagcctc cgccattcca agtcaacact cttcttgagc agaccgtgat ttggaagaga
2701 ggcacctgct ggaaaccaca cttcttgaaa cagcctgggt gacggtcctt taggcagcct
2761 gccgccgtct ctgtcccggt tcaccttgcc gagagaggcg cgtctgcccc accctcaaac
2821 cctgtgggc ctgatggtgc tcacgactct tcctgcaaag ggaactgaag acctccacat
2881 taagtggctt tttaacatga aaaacacggc agctgtagct cccgagctac tctcttgcca
2941 gcattttcac attttgcctt tctcgtggta aagccagta cagagaaatt ctgtggtggg
3001 aacattcgag gtgtcaccct gcagagctat ggtgaggtgt ggataaggct taggtgccag
3061 gctgtaagca ttctgagctg ggcttgttgt ttttaagtcc tgtatatgta tgtagtagtt
3121 tgggtgtgta tatatagtag catttcaaaa tggacgtact ggtttaacct cctatccttg
3181 gagagcagct ggctctccac cttgttacac attatgttag agaggtagcg agctgctctg
3241 ctatatgcct taagccaata tttactcatc aggtcattat ttttacaat ggccatggaa
3301 taaaccattt ttacaaaa
```

TABLE 4

Serine/threonine protein phosphatase from Bacteriophage lambda.
ACCESSION P03772; 221 aa (residues 1-221)

Genomic sequence of bacteriophage lambda is available at Accession numbes J02459 M17233 M24325 V00636 X00906.

REFERENCE 1 (residues 1 to 221); Sanger et al. (1982) Nucleotide sequence of bacteriophage lambda DNA, J. Mol. Biol. 162 (4), 729-773.

amino acid residues 1-221 of lambda serine/threonine protein phosphatase (SEQ ID NO: 22)

```
  1 mryyekidgs kyrniwvvgd lhgcytnlmn kldtigfdnk kdllisvgdl vdrgaenvec
 61 lelitfpwfr avrgnheqmm idglsergnv nhwllngggw ffnldydkei lakalahkad
121 elpliielvs kdkkyvicha dypfdeyefg kpvdhqqviw nrerisnsqn givkeikgad
181 tfifghtpav kplkfanqmy idtgavfcgn ltliqvqgeg a
```

What is claimed is:

1. A method for expressing a recombinant tyrosine kinase domain with reduced phosphorylation, said method comprising co-expressing said recombinant tyrosine kinase domain with a recombinant protein tyrosine phosphatase-1b (PTP1b) phosphatase domain that removes phosphate groups from residues of said tyrosine kinase domain.

2. The method of claim 1, wherein said tyrosine kinase domain and said PTP1b phosphatase domain are expressed in a cellular expression system.

3. The method of claim 2, wherein said tyrosine kinase domain and said PTP1b phosphatase domain are expressed from a bi-cistronic mRNA.

4. The method of claim 2, wherein said tyrosine kinase domain and said PTP1b phosphatase domain are expressed linked as a single fusion protein.

5. The method of claim 2, wherein said tyrosine kinase domain and said PTP1b phosphatase domain are encoded by a single vector.

6. The method of claim 2, wherein said tyrosine kinase domain and said PTP1b phosphatase domain are encoded by separate vectors.

7. The method of claim 1, wherein said tyrosine kinase autophosphorylates.

8. The method of claim 2, wherein said tyrosine kinase comprises the human c-MET kinase domain.

9. The method of claim 2, wherein said tyrosine kinase comprises the human c-Abl kinase domain.

10. A method for expressing a tyrosine kinase enzyme having reduced phosphorylation, comprising co-expressing a recombinant tyrosine kinase enzyme with a recombinant protein tyrosine phosphatase-1b (PTP1b) enzyme that dephosphorylates said tyrosine kinase in a cell.

11. The method of claim 10, wherein said tyrosine kinase and said PTP1b are expressed from a bi-cistronic mRNA.

12. The method of claim 10, wherein said tyrosine kinase and said PTP1b are expressed linked as a single fusion protein.

13. The method of claim 10, wherein said tyrosine kinase and said PTP1b are encoded by a single vector.

14. The method of claim 10, wherein tyrosine kinase and said PTP1b are encoded by separate vectors.

15. The method of claim 10, wherein said tyrosine kinase autophosphorylates.

16. The method of claim 10, wherein said recombinant tyrosine kinase enzyme is phosphorylated by an endogenous enzyme produced by the cell used for expression of said tyrosine kinase enzyme.

17. A cell comprising:
  a first recombinant nucleic acid sequence encoding a tyrosine kinase enzyme subject to enzymatic phosphorylation; and
  a second recombinant nucleic acid sequence encoding a protein tyrosine phosphatase-1b (PTP1b) enzyme that reverses said phosphorylation,
  wherein said first and second recombinant nucleic acid sequences are operatively linked with regulatory sequence(s) such that said first and second recombinant nucleic acids are expressed in said cell.

18. The cell of claim 17, wherein said tyrosine kinase enzyme autophosphorylates when expressed in the cell.

19. The cell of claim 17, wherein said cell is from an *E. coli* strain.

20. The cell of claim 17, wherein said tyrosine kinase enzyme consists essentially of a tyrosine kinase catalytic domain and said PTP1b enzyme consists essentially of a PTP1b catalytic domain, wherein said PTP1b catalytic domain reduces the level of phosphate group modification on said tyrosine kinase catalytic domain.

21. The cell of claim 17, wherein said tyrosine kinase and said PTP1b are expressed linked as a single fusion protein.

22. The cell of claim 17, wherein said tyrosine kinase enzyme and PTP1b enzyme are expressed from a bi-cistronic mRNA.

23. The cell of claim 17, wherein said tyrosine kinase enzyme and PTP1b enzymes are expressed from a single vector.

24. The cell of claim 17, wherein said tyrosine kinase enzyme and PTP1b enzymes are expressed from separate vectors.

\* \* \* \* \*

UNITED STATES PATENT AND TRADEMARK OFFICE
CERTIFICATE OF CORRECTION

| | | |
|---|---|---|
| PATENT NO. | : 7,759,475 B2 | Page 1 of 1 |
| APPLICATION NO. | : 12/409443 | |
| DATED | : July 20, 2010 | |
| INVENTOR(S) | : Brian West | |

It is certified that error appears in the above-identified patent and that said Letters Patent is hereby corrected as shown below:

TITLE PAGE, ITEM (73) ASSIGNEE:

"(73)   Assignee:  Plexxikon, Inc., Berkeley, CA (US)", should read,

--(73)  Assignee:  Plexxikon Inc., Berkeley, CA (US)--

Signed and Sealed this
Fifth Day of June, 2012

David J. Kappos
*Director of the United States Patent and Trademark Office*